(12) United States Patent
Robertson et al.

(10) Patent No.: US 7,438,228 B2
(45) Date of Patent: Oct. 21, 2008

(54) SYSTEMS AND METHODS FOR MANAGING ELECTRONIC PRESCRIPTIONS

(76) Inventors: Scott Robertson, 1024 S. Aurens, Lombard, IL (US) 60148; Robert Robertson, Jr., 274 Hagans Ave., Elmhurst, IL (US) 60126; Harikrishna Madanaraj, 1765 St. Ann Dr., Hanover Park, IL (US) 60133; Marappan Ramachandran, 1274 Strawberry Ct., Bartlett, IL (US) 60103

( * ) Notice: Subject to any disclaimer, the term of this patent is extended or adjusted under 35 U.S.C. 154(b) by 93 days.

(21) Appl. No.: 11/418,961

(22) Filed: May 5, 2006

(65) Prior Publication Data

US 2006/0261145 A1  Nov. 23, 2006

Related U.S. Application Data

(60) Provisional application No. 60/677,858, filed on May 5, 2005.

(51) Int. Cl.
*G06F 19/00* (2006.01)
*G06Q 30/00* (2006.01)
*G06Q 90/00* (2006.01)

(52) U.S. Cl. .................. 235/385; 235/375; 235/487; 235/382; 705/26

(58) Field of Classification Search ............ 235/385, 235/487, 486, 485, 375, 382, 383; 705/26, 705/28
See application file for complete search history.

(56) References Cited

U.S. PATENT DOCUMENTS

| | | | |
|---|---|---|---|
| 2003/0158755 A1* | 8/2003 | Neuman | 705/3 |
| 2005/0108046 A1* | 5/2005 | Craft | 705/2 |
| 2005/0144038 A1* | 6/2005 | Tamblyn et al. | 705/2 |
| 2006/0235726 A1* | 10/2006 | Paraison et al. | 705/2 |
| 2006/0259330 A1* | 11/2006 | Schranz | 705/3 |

* cited by examiner

*Primary Examiner*—Edwyn Labaze
(74) *Attorney, Agent, or Firm*—Cardinal Law Group

(57) ABSTRACT

A method for managing prescriptions includes receiving a patient assessment from a physician at an application server, receiving a prescription based on the patient assessment, determining drug interactions based on the received prescription, sending the prescription to a pharmacy based on the drug interaction determination and validating the prescription. Validating the prescription comprises a three-way match of prescription information stored on a centralized database with the filled medicine container and the bulk container. Prescriptions can be prescribed and patient records reviewed using remote devices linked to the prescription management application server and centralized database.

16 Claims, 12 Drawing Sheets

600

600

SYSTEMS AND METHODS FOR MANAGING ELECTRONIC PRESCRIPTIONS

RELATED APPLICATION

This application claims priority to U.S. Provisional Application No. 60/677,858 titled "Systems and Methods for Managing Electronic Prescriptions," to Scott Robertson, et al., filed May 5, 2005, the entirety of which is incorporated herein by reference.

TECHNICAL FIELD OF THE INVENTION

The present invention relates to systems and methods for managing and processing electronic prescriptions and building a centralized prescription database.

BACKGROUND OF THE INVENTION

When a physician orders a prescription from a remote location using a cell phone, significant patient information and interactions to current medication is not available. In addition, the physician is calling the pharmacy and talking to the pharmacist, taking the pharmacist's attention away from filling prescriptions. During the phone call, the pharmacist asks the physician for their DEA number to validate their identity. This ID can be obtained by those not licensed to prescribe medications. As a matter of fact, many times the DEA number is pre-printed on the physician's prescription pad. Current studies note that in 2004 nearly 2 million prescriptions were filled incorrectly by a pharmacy. Many times, these errors resulted in results not desired by a health care professional. This current manual process is prone to errors and exposes the patient, physician, and pharmacist to unnecessary physical and financial risks.

From the physician's and pharmacist's perspective, these risks and inefficiencies are key drivers that raise the cost of insurance. From a patient's perspective, confidence in the process will increase patient satisfaction. Moreover, the more decentralized patient information is, the more difficult it is to drive efficiencies that can lower overall medical costs.

Therefore, it would be desirable to improve management of patient medications by improving a physician's and pharmacist's ability to securely and safely prescribe, transmit, and fill patient prescriptions.

SUMMARY OF THE INVENTION

One aspect of the invention provides a method for managing prescriptions. The method includes receiving a patient assessment from a physician at an application server, receiving a prescription based on the patient assessment at the application server, determining drug interactions at the application server based on the received prescription, sending the prescription from the application server to a pharmacy based on the drug interaction determination and validating the prescription based on the sent prescription and patient assessment.

Another aspect of the invention provides a method for managing prescriptions that includes receiving a prescription from an application server at a pharmacy, filling the prescription at the pharmacy; comparing the filled prescription to a bulk medicine container, and comparing the filled prescription to the received prescription and providing the filled prescription to a customer based on the comparison to the bulk medicine container and received prescription.

Another aspect of the invention provides a system for managing prescriptions. The system includes means for receiving a patient assessment from a physician at an application server, means for receiving a prescription based on the patient assessment, means for determining drug interactions based on the received prescription, means for sending the prescription to a pharmacy based on the drug interaction determination and means for validating the prescription.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The drawings are not to scale. The foregoing aspects and other attendant advantages of the present invention will become more readily appreciated by the detailed description taken in conjunction with the accompanying drawings.

DETAILED DESCRIPTION OF THE PREFERRED EMBODIMENT

Reference will now be made in detail to exemplary embodiments of the invention, examples of which are illustrated in the accompanying drawings. Wherever possible, the like reference numbers will be used throughout the drawings to refer to like elements.

Figure 1:
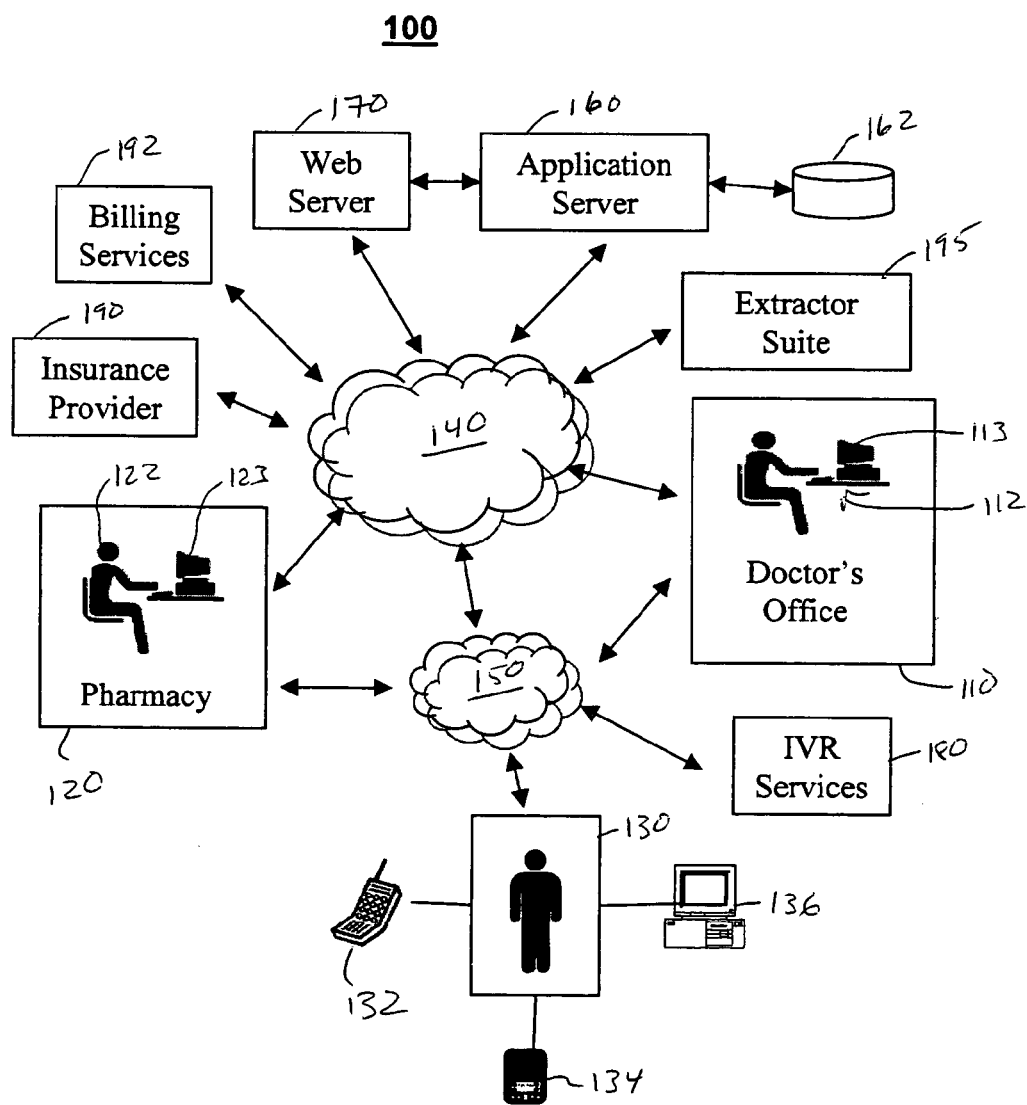
FIG. 1 is a schematic illustration of one embodiment of a prescription management system in accordance with the present invention.

FIG. 1 is a schematic diagram of one embodiment of a prescription management system 100, in accordance with the present invention. Prescription management system 100 provides the tools necessary for a physician to review prescriptions and securely transmit prescriptions electronically. System 100 also allows pharmacies to validate prescriptions prior to providing the filled prescription to the patient. System 100 includes health care provider 110, pharmacy 120, physician 130, network 140, communication network 150, application server 160 and web server 170.

Network 140 provides communications between the various components of system 100. Network 140 may be implemented through any suitable combination of wired and/or wireless communication networks. Network 140 may be a shared, public, or private network and encompass a wide area or local area. By way of example, network 140 may be implemented through a wide area network (WAN), local area network (LAN), an intranet, or the Internet. Web server 170 and application server 160 are connected to network 140. In addition, web server 170 or application server 160 may access other services such as billing services 192 and insurance provider services 190 via network 140.

Communication network 150 is implemented as any suitable system or collection of systems for connecting communication devices such as phone 132, personal digital assistant (PDA) 134 and personal computer 136 to network 140. Phone 132 may be implemented as a wired or wireless communication device as are known in the art. Communication network 150 includes land and wireless carrier systems for connecting wired and wireless communication devices to network 140. In one embodiment, communication network 150 connects at least one wireless carrier system to at least one land network. Communication network 150 includes a public-switched telephone network (PSTN) land network. In another embodiment, land network is implemented as an Internet protocol (IP) network. In other embodiments, the land network is implemented as a wired network, an optical network, a fiber network, or any combination thereof. Communication network 150 connects medical service provider 110, pharmacy 120 and physician 130 to web server 170 and application server 160 via network 140.

System 100 includes at least one medical services provider 110 and at least one pharmacy 120. Medical services provider 110 and pharmacy 120 include workstations 112 and 122, respectively. Workstations 112 and 122 allow a user to exchange information with application server 160 via web server 170. Workstations 112 and 122 comprise at least one terminal 113, 123. Terminals 113, 123 may be any type of appropriate device for communicating with application server 160 over network 140. Terminal 113, 123 may be a tablet notebook, a personal computer (PC), or the like, having hardware and software for running a program for communicating with application server 160. Terminal 113, 123 includes a computer usable medium to execute Internet browser and Internet-access computer programs for sending and receiving data over communication network 150 to web server 170. In one embodiment, terminal 113, 123 includes hardware and software for running a web browser for communicating with web server 170 and/or application server 160 via network 140. Users may access application server 160 via network 140 through a web browser or software running on, for example, terminal 113, 123. Terminals 113, 123 include graphical user interfaces that present the user with a series of screens prompting the user to make various selections and input various patient related data. The graphical user interfaces are discussed in more detail below.

Terminals 113, 123 send patient related data to application server 160 through a web-page interface using communication standards such as hypertext transport protocol (HTTP), and transport-control protocol and Internet protocol (TCP/IP). Patient related data from client-side software is transmitted to server-side software of application server 160.

System 100 further includes a centralized database 162 operably connected to application server 160. Centralized database 162 comprises a database schema running a database, such as an industry standard relational database management system as are known in the art. Centralized database 162 comprises a database for storing a plurality of electronic medical records comprising patient related data. Centralized database 162 includes patient related data from a plurality of patients. Patient related data includes, but is not limited to, patient medical history data, prescription data, patient personal data, patient insurance data and patient billing data. Use of a prescription management service having a centralized database to store patient medical records provides a real-time view of the patient medical records.

In one embodiment of system 100, Really Simple Syndication (RSS) technology is used in the software and methods for managing electronic prescriptions. In use, rather than faxing prescriptions, RSS is used to retrieve prescriptions in the pharmacy. The prescriptions are generated out of the application server 160 by creating a PDF and placing on the web server hardware. When the pharmacy logs into the application, the prescriptions are sent to the browser of the pharmacy. Use of RSS reduces the amount of additional software that needs to be placed on the users computer.

In another embodiment, various components of system 100 include hardware and software for instant messaging between terminals 113 and 123 and/or between terminals 113, 123 and PDA 134.

Figure 2:
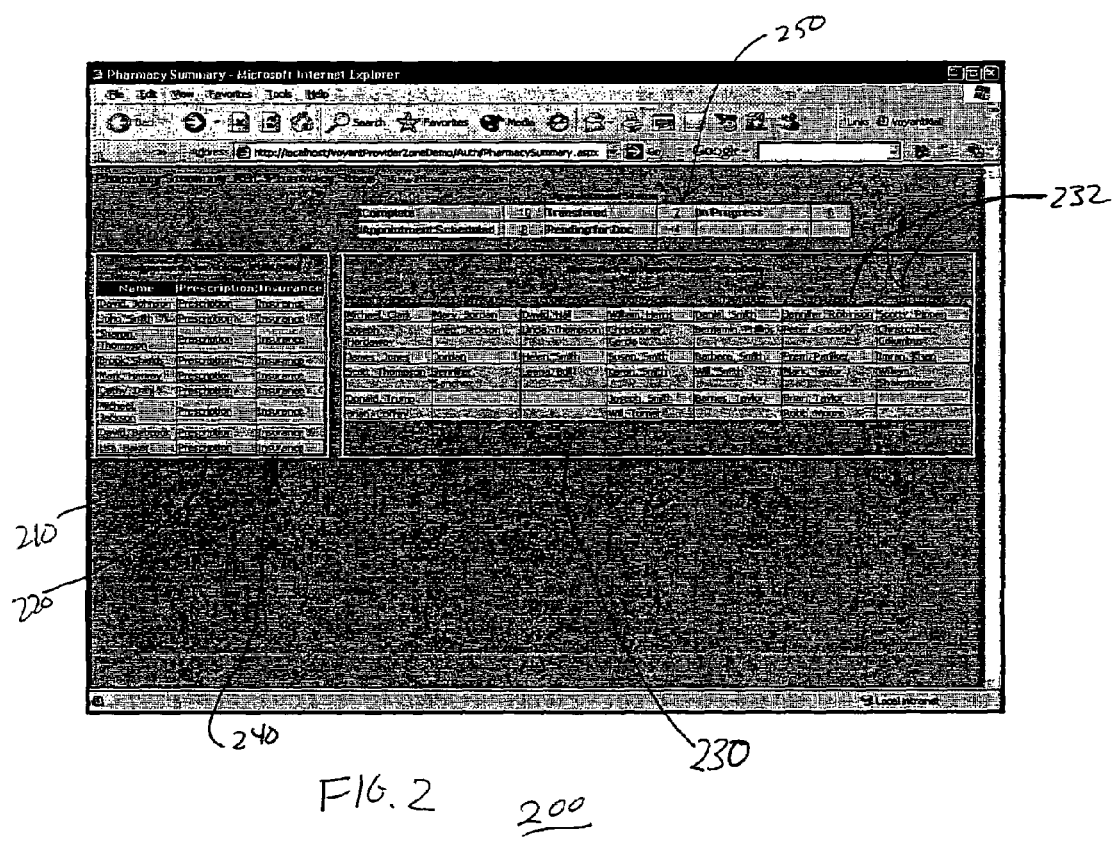
FIGS. 2 to 7 illustrate graphical user interfaces for use in the prescription management system illustrated in FIG. 1.
Figure 3:

FIGS. 2 and 3 show exemplary screenshots which make up the pharmacy graphical user interface (GUI) 200 located on terminal 123. Pharmacy GUI 200 provides various information to the pharmacists and pharmacy technicians that enable the pharmacists and pharmacy technicians to manage workflow for the pharmacy. In use, the pharmacy GUI 200 provides and displays information to the pharmacists and pharmacy technicians relating to a plurality of patient prescriptions. The pharmacy GUI allows a pharmacist to view all work that needs to be completed for each day. Pharmacy GUI 200 illustrated in FIG. 2 displays a list of patients 210 and the related prescriptions 220 that are pending. GUI 200 also displays a schedule of pending prescriptions 230. Daily schedules 232 are displayed with links to patient detail information and insurance information 240. In one embodiment, the pharmacy GUI includes a 7-day view of work that is coming into the pharmacy. Pharmacy GUI 200 also includes a status indicator field 250 that displays the status of prescriptions. Pharmacy GUI 200 provides data entry fields to, for example, input patient related prescription data and update the status of the pending prescriptions. In one embodiment, the pharmacy GUI 200 also provides a daily schedule 270 for the pharmacy that displays the open orders in chronological order. There are also links 272 to patient contact information for each order for a designated timeslot. Those with skill in the art will recognize that the pharmacy GUI 200 may display a variety of information pertinent to processing prescriptions that is not illustrated in FIGS. 2 and 3.

Figure 4:
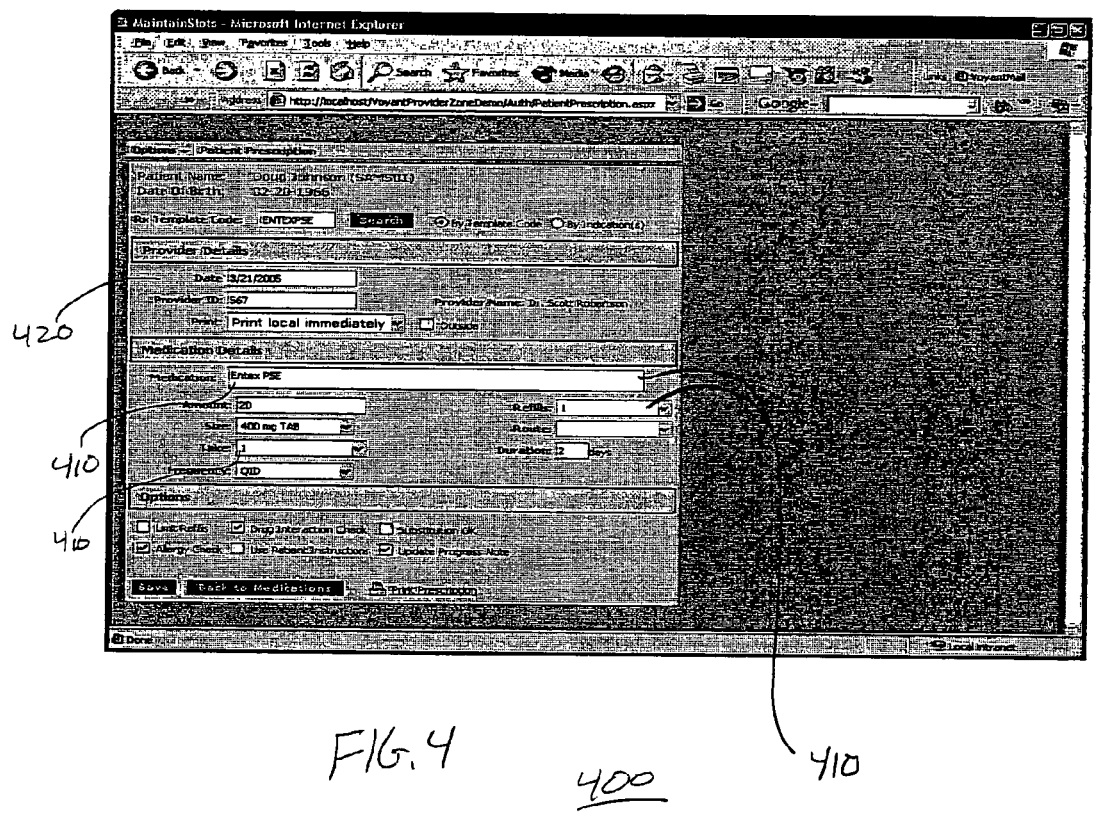

FIG. 4 is an exemplary screenshot showing the web page physician GUI 400 the physician uses to create the prescription. Physician GUI 400 provides input fields 410 the physician fills in with information relating to the patient prescription. Input fields include, but are not limited to, medication, amount, size, number to take, frequency, refills, and duration. There are also optional input fields the physician may use to provide additional information or to take a certain action regarding the patient prescription. In an example, physician GUI 400 may include action fields that indicate that the prescription should be cross-checked for allergic reactions and drug interactions. Input fields may also provide information to limit the number of refills and that substitutions of the prescribed medication are allowed. In one embodiment, physician GUI 400 also includes input fields 420 for adding and associating a provider (physician) ID to the patient prescription. Those with skill in the art will readily recognize that the physician GUI may include additional input fields for preparing a patient prescription that are not illustrated in FIG. 4. For example, the physician GUI may also include input fields for the particular pharmacy location the patient prefers for processing the prescription. In one embodiment, the prescription is automatically sent to the preferred location to begin processing.

Figure 5:
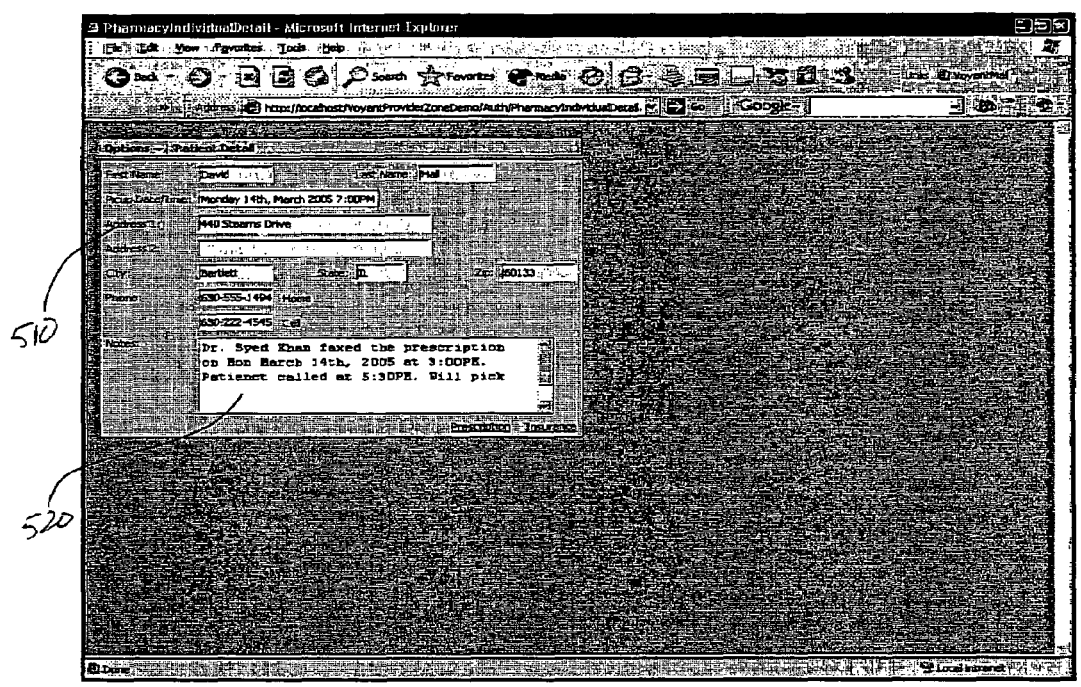
Figure 6A:
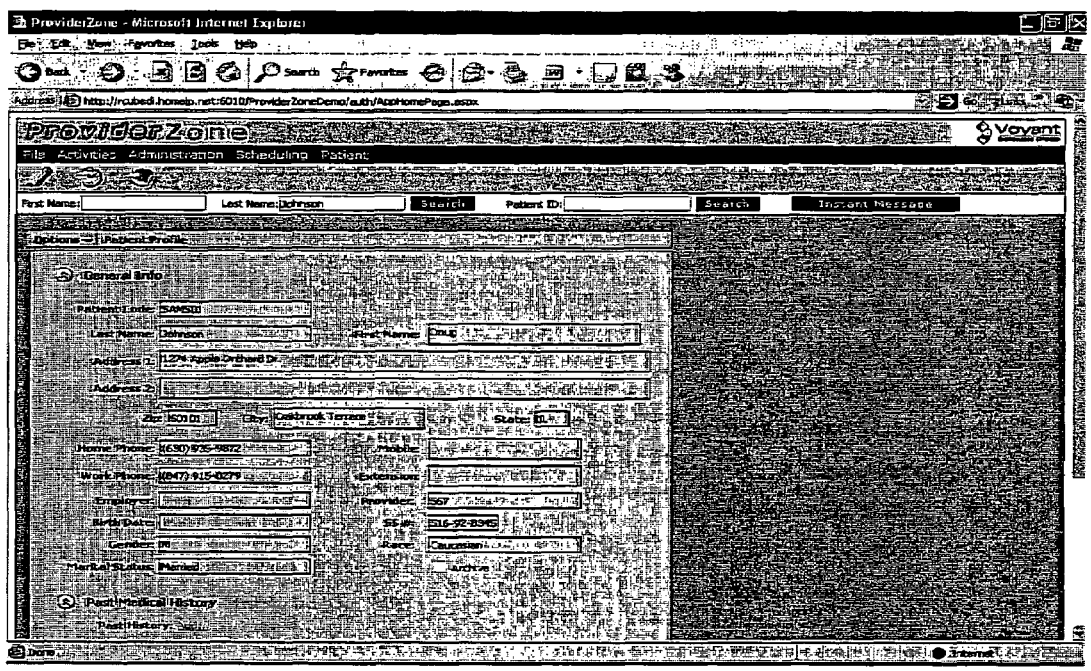
Figure 6B:
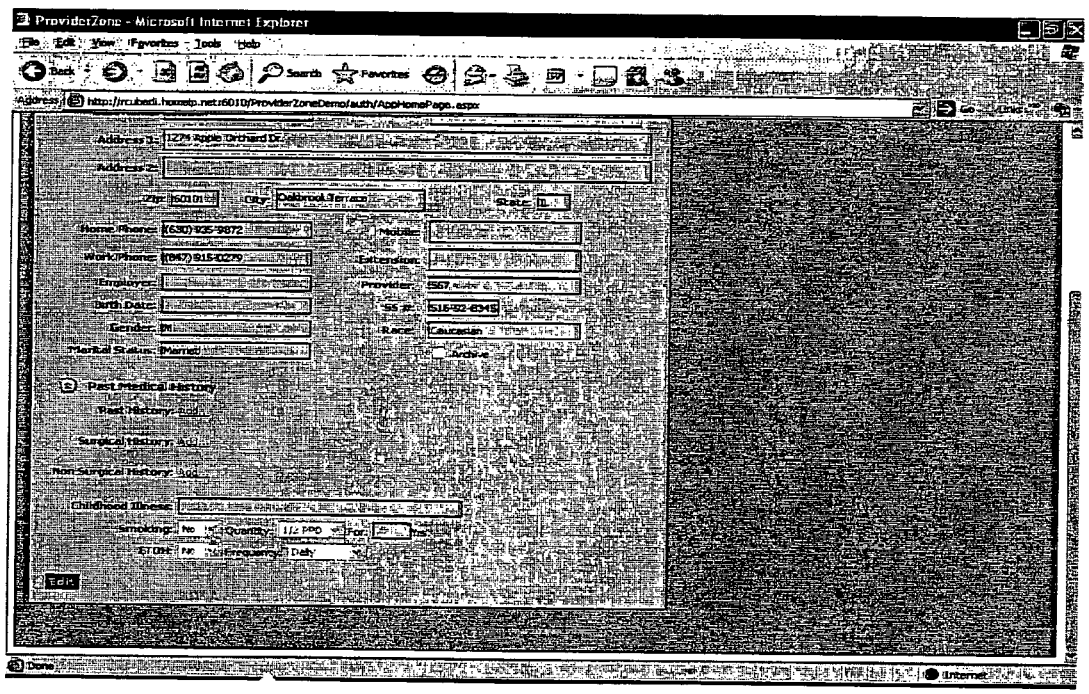

FIGS. 5, 6A, and 6B are exemplary screenshots that show patient data that may be input into and displayed on a physician GUI. FIG. 5 illustrates a GUI 500 that displays patient contact information 510 and notes 520 relating to the patient and/or patient prescription. FIG. 6A a GUI 600 that displays patient information such as name, address, home and cell phone numbers as well as specific instructions from the physician. This GUI may be accessed by the pharmacy as needed during the processing of the patient prescription. FIG. 6A shows additional personal patient information such as gender, marital status, SSN, and race. In one embodiment the patient information includes a unique patient identifier which may be used by medical personnel or other authorized users to access the patient's medical records. In one embodiment, the unique patient identifier comprises the patient's social security number. In another embodiment, the patient unique identifier comprises a combination of alphanumeric characters assigned to the patient. This GUI may also be accessed by the pharmacy. FIG. 6B shows additional information about past medical/surgical, and childhood illnesses.

Figure 7:
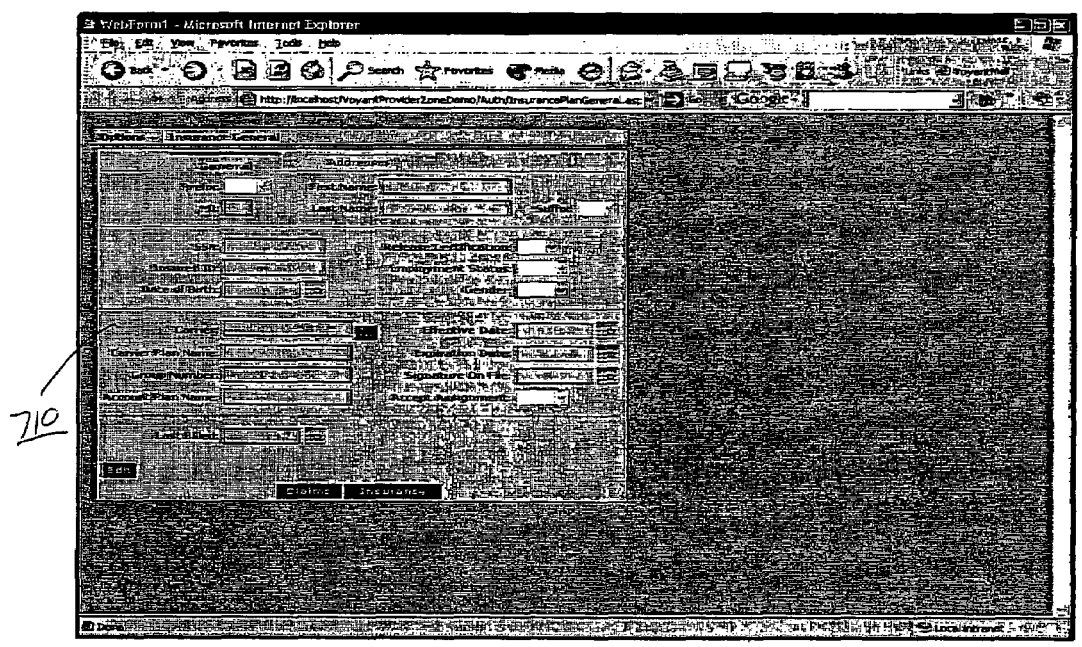

FIG. 7 is an exemplary screenshot showing a GUI 700 used to create and view insurance information 710. Information displayed is name, SSN, insurance ID, date of birth (DOB), effective date, insurance carrier, carrier plan, group number, account plan name.

In practice, the pharmacy GUI contains all patient prescriptions ordered by physicians that are to be processed by the pharmacy. In one embodiment, the prescriptions are sent automatically via network 140 to the patient's preferred pharmacy. Sending the prescription to the pharmacy as soon as the prescription is written eliminates the need for the pharmacy having to wait until the patient shows up to start processing the prescription. In one embodiment, application server 160 uses a "pull" model as the work is pulled into a browser when the pharmacy logs into system 100 web application 170 and connects to the centralized database 162.

In one embodiment, each transaction and or input into the system via either the physician GUI or pharmacy is logged with a date and time stamp and an access code or user ID providing an audit trail of all transactions performed using system 100.

Figure 8:
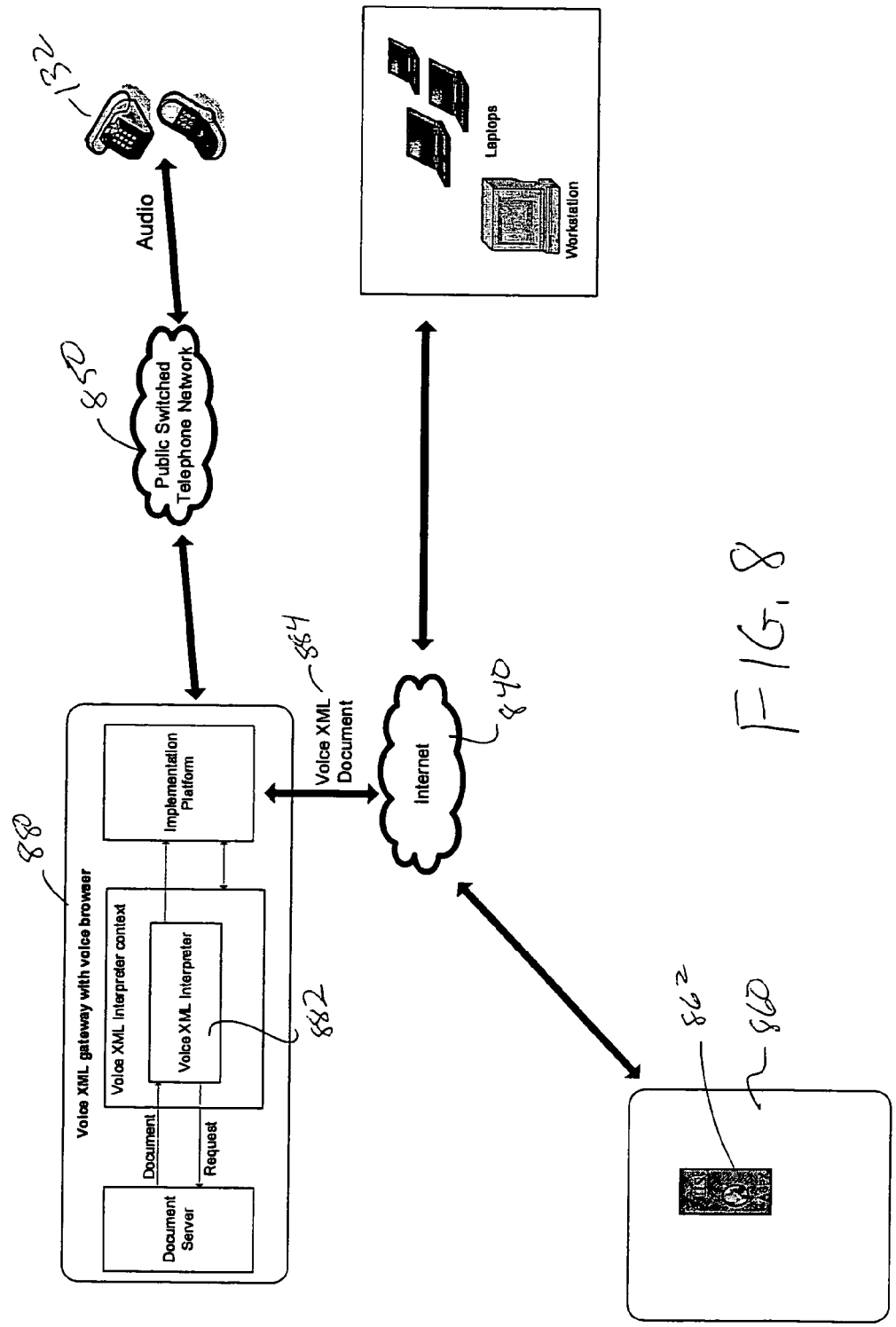
FIG. 8 is a schematic illustration of one embodiment of an interactive voice response system for use in the prescription management system illustrated in FIG. 1.

Prescription management system 100 also includes Interactive Voice Response (IVR) services 180. FIG. 8 is a diagram of an exemplary technical architecture 800 for supporting IVR services 180 of system 100. Audio from the handheld device 132 is transmitted over a public switched telephone network 850 to a Voice XML gateway 880 with a voice browser running a voice XML interpreter 882. XML interpreter 882 converts the audio into Voice XML documents 884. Voice XML documents 884 are transmitted via the Internet 840 to the application server 860 running ASPX pages 862 within IIS. Information generated from application server 860 is sent to the Voice XML gateway 880 and converted into audio and sent back to the physician through the public switched telephone network 850. This functionality may be run on proprietary hardware or a hosted solution.

Prescription management system 100 provides the primary care physicians and any specialists the ability to prescribe medications for patients, direct the prescription to a preferred pharmacy and view the status of prescriptions. Prescription management system 100 allows physicians and pharmacists to integrate the prescribing and filling of medications into one system. Prescription management system 100 provides a real-time view into patient prescriptions, real-time ability to view, make and reserve a repair appointment for the customer, an ability to e-mail repair appointment details and an appointment confirmation to the customer, one-click access to a customer's scheduled appointments, claim status, store information, and a progress bar to view the status of a repair, including an expected completion date.

Figure 9:
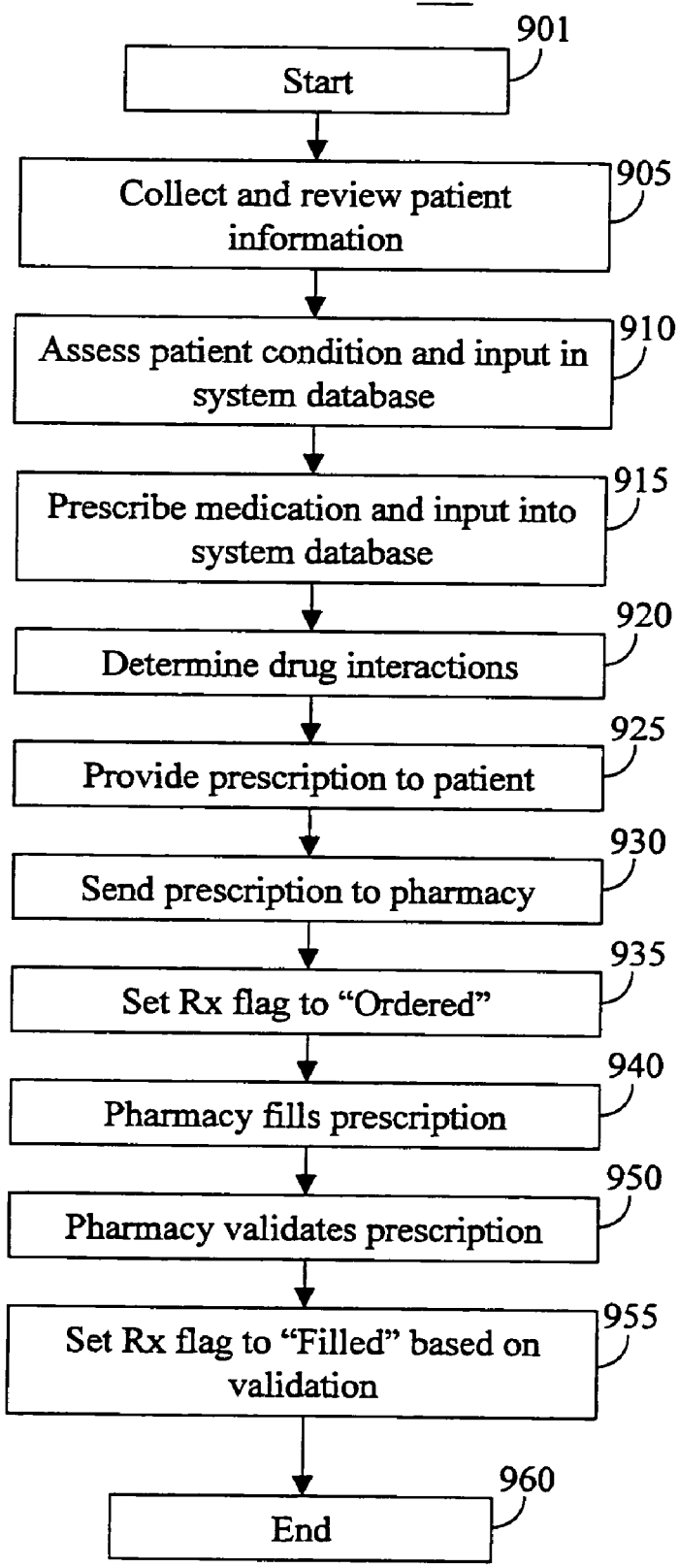
FIG. 9 is a flow chart illustrating a method of managing prescriptions, in accordance with the present invention.

FIG. 9 is a flow diagram illustrating one embodiment of a prescription management method 900, in accordance with the present invention. In one embodiment, method 900 is implemented using prescription management system 100. Method 900 begins at step 901. A physician begins by collecting and reviewing patient information that may include information regarding the patient's illness or condition and medical history (Step 905). The collected information may also include all aspects of the physician's SOAP protocol, historical and/or relevant family information, surgeries, and so on. The physician makes an assessment and, using a physician GUI, inputs all information into a system database 162 via an application server 160 (Step 910). Physician GUI may be similar to or the same as those illustrated in FIGS. 5-7. Based on the assessment, the physician prescribes medication and inputs the prescription(s) details into system 100 centralized database 162 using a physician GUI such as physician GUI 400 illustrated in FIG. 4, (Step 915).

At step 920, the physician reviews drug interactions through application 160. In one embodiment, drug interactions are reviewed automatically based on an input selection made by the physician at the time of preparing the prescription. Drug interactions may be reviewed by comparing the currently prescribed medication(s) to any previously prescribed medication whose details are included within the patient's medical history stored on centralized database 162. Based on the drug interaction review, a prescription is printed with a UPC and barcode of the medication and given to the patient (Step 925). In addition, the prescription is sent to the preferred pharmacy as indicated by the patient (Step 930). The prescription may be transmitted to the pharmacy in any manner, such as, for example, by fax, email, or electronic data interface (EDI). In another embodiment, a PDF is created and stored on the centralized database 162 and is accessible by pharmacy personnel. The choice of transmission may be configured at the time the prescription is prepared and the pharmacy location that was chosen. At step 935 the physician sets the prescription status indicator flag to "Rx Ordered" via the physician GUI.

Pharmacy logs into the application server 160 via web server 170 to access and view patient prescriptions yet to be filled (Step 940). The pharmacy access application server 160 using the pharmacy GUI such as pharmacy GUI illustrated in FIGS. 2-3. At step 945, the pharmacy starts the prescription filling process. In one embodiment, the prescription filling process is started by scanning a bar code located on the printed prescription received by any one of those means described above such as, for example, by fax or email. In another embodiment, the filling process starts by scanning a bar code located on the prescription presented to the pharmacy by the patient. The received prescription is then filled (Step 945).

Next, the filled prescription is validated (Step 950). In one embodiment, the validation comprises a three-way matching process to ensure that the medication contained in the filled container is the medication prescribed by the physician. To validate the prescription, the pharmacy scans a UPC barcode or RSS (Reduced Space Symbology) designation contained on the bulk medication container and compares the information related to that UPC barcode or RSS with the information related to a barcode on the filled prescription container. The comparison will determine if the medication contained in the filled container matches the medication of the bulk container. If the information matches, then the validation continues by comparing the container barcodes to the prescription information contained in the centralized database. To make this next comparison a validation request is generated using the pharmacy GUI and sent to the application server 160. To validate the prescription, the patient medication as filled is compared to the prescription information stored on the centralized database 162. Based on a successful validation response received from the application server, a final transaction is sent to the application server to set the prescription status flag to "Rx Filled" and the prescription is removed from the workload queue displayed on the pharmacy GUI (Step 955). In one embodiment, when each prescription is filled, an update request from the application server is invoked to add the filled medication to a list of current medications being taken by the patient. Method 900 ends at step 960.

Figure 10:
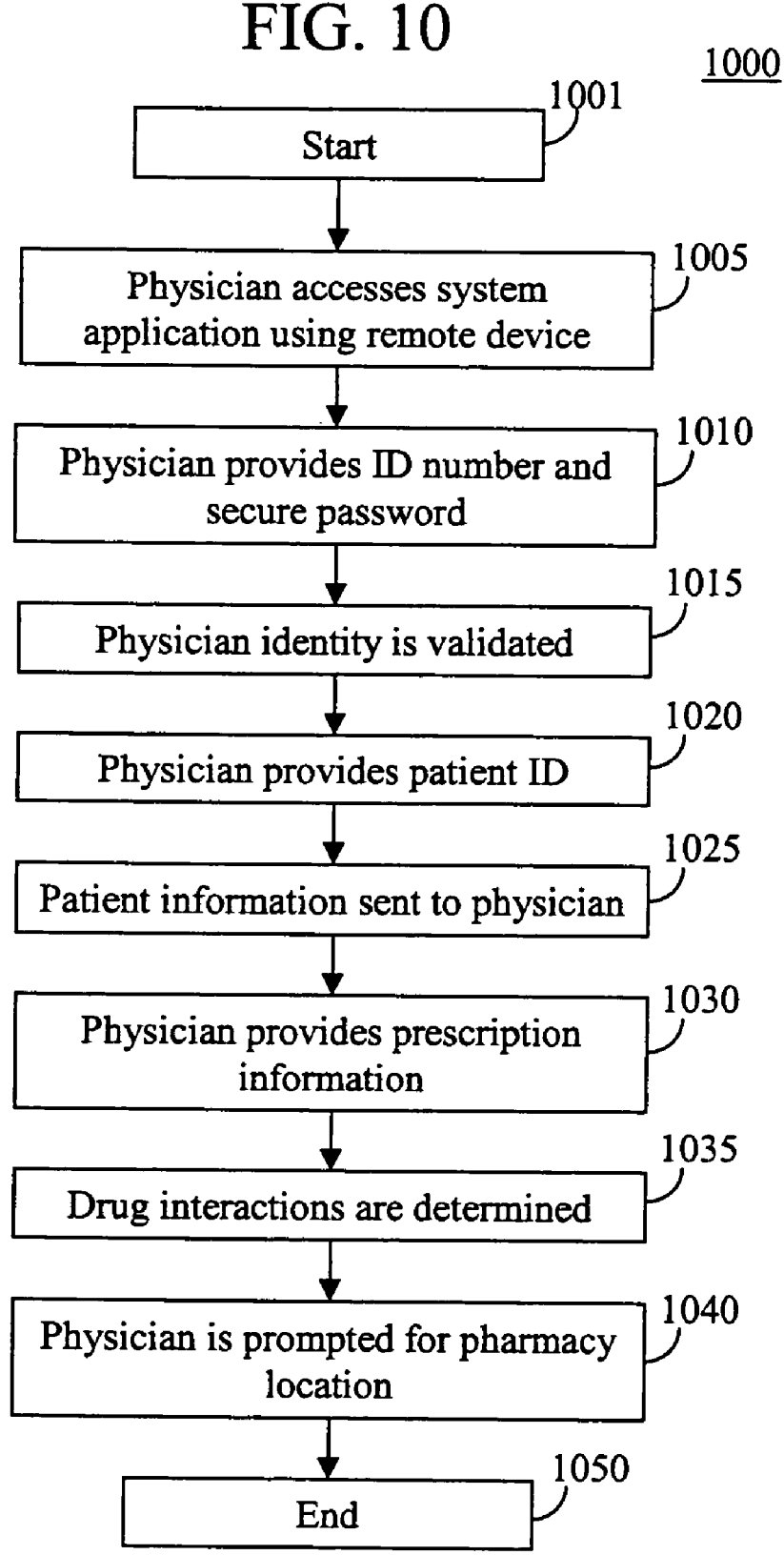
FIG. 10 is a flow chart illustrating another method of managing prescriptions, in accordance with the present invention.

FIG. 10 illustrates another method 1000 for managing and processing electronic prescriptions, in accordance with the present invention. Method 1000 may be implemented using prescription management system 100 illustrated in FIG. 1. A physician uses method 1000 to call in a new prescription or renew a previous prescription for a patient using a remote device. Method 1000 begins at step 1001.

At step 1005, a physician accesses the prescription management application server using a remote device. In one embodiment, the physician sends an access request to the application server. The physician may access the application server using a phone such as a landline phone or a mobile phone or a PDA. In those embodiments where the physician uses a phone, method 1000 utilizes the IVR services as described above and illustrated in FIG. 8 to access the prescription management application server. In these embodiments, the information is provided by the physician by speaking into a microphone located on the device. In those embodiments where the physician uses a wireless hand held device running a browser, for example a PDA, the PDA includes software and hardware for running a program capable of communicating with the application server 160 through web server 170. The physician begins by launching a website on the PDA. In these embodiments, the information is provided by the physician using the device keypad or other input device. In one embodiment, the application sends an prompt for an identification number and or a password.

The physician next provides an assigned DEA number and/or a secure password to application server 160 (Step 1010). The DEA number and secure password may be provided by speaking the number and password or by entering the number and password using the device keypad. At step 1015 the physician identity is validated based on the received DEA number and secure password. Upon validation, the physician provides a patient ID (Step 1020). The patient ID may be the patient's SSN or other unique identifier as described above. Based on the received patient ID, patient information is sent to the physician from the application server (Step 1025). Patient information includes current medications, allergies, and other relevant information as configured in the application server and stored in the centralized database. In one embodiment, the patient data is encrypted to provide a secure transmission of the data from the centralized database to the PDA.

Next, based on the received information, the physician provides prescription information to the application server (Step 1030). Prescription information includes, but is not limited to, the desired medication, dosage, frequency, and number of refills. Based on the provided prescription information, application server 160 searches the patient information to determine drug interactions (Step 1035). Any determined drug interaction is transmitted to the physician for review. Alternatively, if no drug interaction is found, a message to that effect is transmitted to the physician.

The physician is then prompted for a pharmacy location to send the prescription to for processing (Step 1040). If a default pharmacy location is selected by the physician, the physician can terminate the call. If the default location is not where the patient wished the prescription to be sent, the physician must call the requested pharmacy to provide the prescription information. The processing of the prescription is implemented as described above in regards to Steps 930 to 955 of method 900 illustrated in FIG. 9. Method 1000 ends at Step 1050.

Referring to again to FIG. 1, system 100 may also include an extractor suite 195. Extractor suite 195 provides a practice the ability to build and accumulate prescription information for physicians who do not have the prescription management application. The extractor suite 195 is a non-intrusive mechanism that monitors the prescription traffic and builds a centralized prescription database for a given practice. The extractor suite 195 consists of components that have the ability to extract key information from the prescriptions prescribed by the doctors to the patients. The extractor suite 195 is installed within a physician's computer that runs a competing EMR component and extracts information from a prescription prescribed by the physician.

This extraction allows for the creation of centralized prescription records in the centralized database for competing EMR applications. When a prescription is faxed or printed through the competing EMR application, an extractor suite component will parse through the print or fax server, searching for and logging relevant information about the patient, medication, pharmacy and physician. When this information is detected, a transaction is generated to update the centralized database with all of the information gathered. The benefit of this component is that it can create a complete view of prescriptions for a pharmacy for a given practice.

Figure 11:
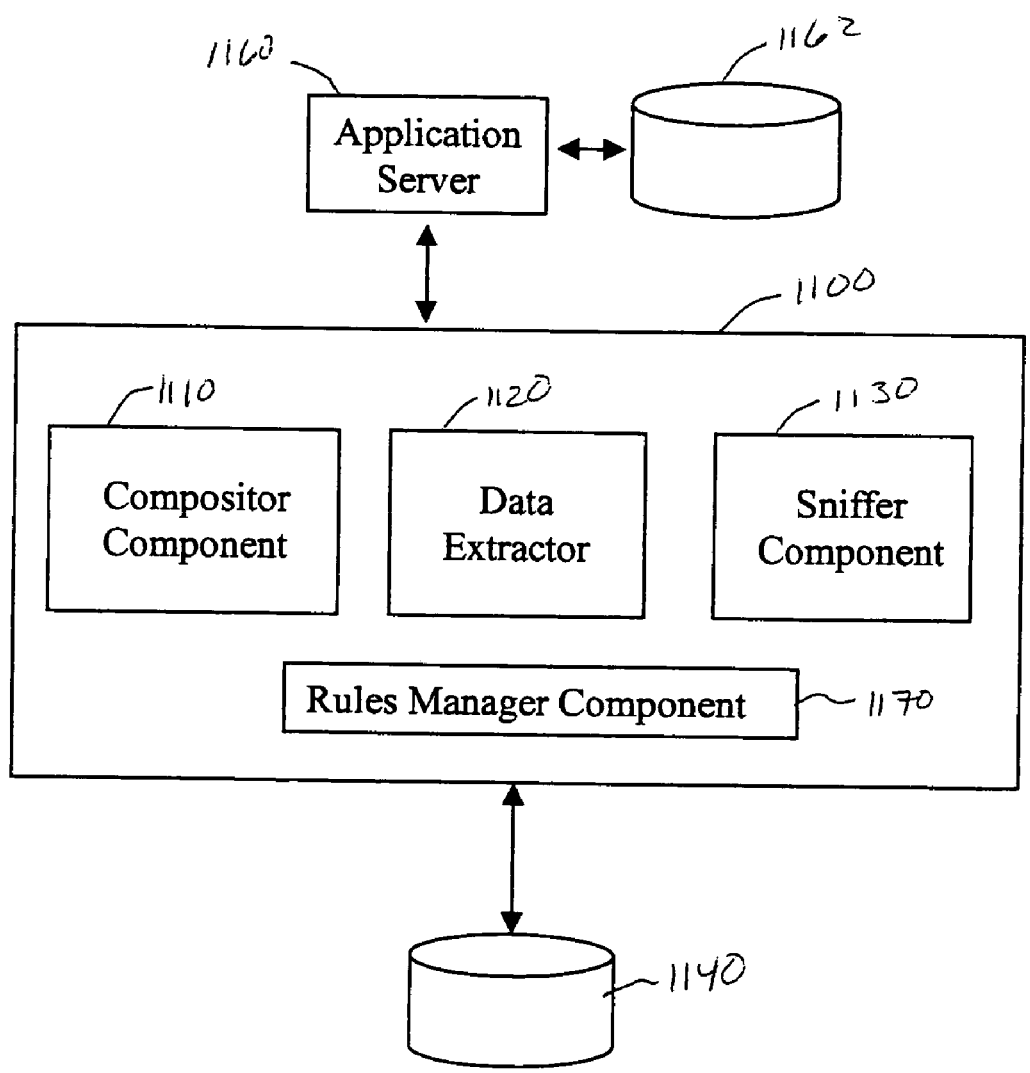
FIG. 11 is a schematic illustration of an extractor component illustrated in FIG. 1.

FIG. 11 illustrates one embodiment of an extractor suite 1100. Extractor suite 1100 includes a compositor component 1110, a data extractor 1120 and a sniffer component 1130. Extractor suite 1100 is operable connected to competing EMR database 1140. Extractor suite 1100 is connected to application server 1160 via a network such as network 140 of system 100. A centralized database 1162 is operably connected to application server 1160. Application server 1160 and centralized database 1162 may be the same as or similar to application 160 and centralized database 162 illustrated in FIG. 1. The extractor suite 1100 enables disparate EMR applications to create centralized database records for electronic prescriptions. The allows for more extensive prescription information from more locations to be centrally located for complete practices and pharmacy chains.

Sniffer component 1130 monitors the TCP/IP packets that are associated with the prescription. Sniffer component 1130 inspects the TCP/IP traffic and identifies the packets associated with a given prescription when either the physician sends a prescription to the printer or to the pharmacy (via facsimile). When installed on a computer running the competing EMR component sniffer component 1130 identifies what the protocol is and based on the rules configured via a rules manager will inspect the traffic either to the printer or fax server and pass the information to the compositor component 1110. When installed within a fax server or the print server the component will inspect the incoming traffic and perform the same steps as specified above to extract the packets associated with a prescription.

Compositor component 1110 rebuilds the prescription from the TCP/IP packets. Compositor component 1110 takes the packets associated with a prescription and reconstructs the information into a text file. Responsibilities of the compositor component 1110 include error detection, and correction of the TCP/IP stream and composition of packets belonging to a prescription. The text file will be created by extracting key information from the prescription based upon the rules configured within the rules manager. In one embodiment, the text file created from this point on will have the same format across all the practice facilities. Compositor component 1110 will use positional matches and pattern analysis to create the text files from the packets. The key information that will be extracted and will be available within the text file includes, but is not limited to, patient name, patient date of birth, prescription date, medicine prescribed, physicians ID, physicians practice information, physicians name, pharmacy information, and dosage information.

Data extractor component 1120 monitors the creation of the text files created by the compositor component 1110. Once data extractor component 1120 has detected that a new text file has been created it will extract the information from the text file using positional matches and pattern analysis. Once extracted, the information will then be added to the centralized database 1162 along with other tracking information pertinent to the prescription. In one embodiment, once available within the centralized database 1162 the application server will takeover in transmitting the prescription in preparation for filling and prescription validation as described above and illustrated in FIG. 9.

A rules manager component 1170 is also associated with extractor suite 1100. Rules manager component 1170 includes all the metadata required to configure the extractor suite 1100 for a specific EMR vendor. The metadata includes information such as: fax and print server IP address; the template of a given prescription sent to the fax or print server; positional information of the key data available within the prescription; format of the text file created by the compositor components; and positional information of the text file to be used by the data extractor component.

In other embodiments, system 100 may be accessed by specialists, after the primary care physician provides an electronic referral and real-time patient information for a referral to a specialist. An electronic referral is sent to the specialist along with a secure user ID and password that expires after the date of the referral. When the application server 160 is accessed by the specialist in their office, or via a wireless handheld device, the specialist physician is prompted for a user ID and password and also their DEA number to validate they are actually the specialist that was referred to. The specialist is able to access specific parts of the patient's electronic medical records stored on the centralized database 162. This reduces redundant questions for the patient and specialist, allowing for additional time for the specialist to evaluate and manage the patient's condition. A new progress note may be added by the specialist and stored on the centralized database. If medications are prescribed, they are also logged on the centralized database. This information can then be accessed by the primary care physician. If a medication is prescribed by the specialist, the specialist may print out a bar coded script to give to the patient or the prescription can be sent electronically to a participating pharmacy and then be accessed by the pharmacy as described above.

System 100 can also be integrated with other physician practice management systems such as scheduling and billing. In one embodiment, the application is written using open standards to enable web services. Preferably, systems and methods consistent with this invention are sufficiently flexible to allow use by pharmacies, physicians, and insurance companies to view medication selections, prescription status, and manage workloads. Such systems and methods can also accommodate other partners of physicians, such as an oversight group charged with quality assurance such as Joint Commission, or a pharmacy benefit managers providing services for health insurers. Additionally, such systems and methods can also allow patients to access a secured website directly to request a refill of a long-term medication and check status information on their prescription.

The foregoing descriptions of the invention have been presented for purposes of illustration and description. They are not exhaustive and do not limit the invention to the precise form disclosed. Modifications and variations are possible in light of the above teachings or may be acquired from practicing of the invention. For example, the described implementation includes software but the present invention may be implemented as a combination of hardware and software or in hardware alone. Additionally, although aspects of the present invention are described as being stored in memory, one skilled in the art will appreciate that these aspects can also be stored on other types of computer-readable media, such as secondary storage devices, like hard disks, floppy disks, or CD-ROM; a carrier wave from the Internet or other propagation medium; or other forms of RAM or ROM. The scope of the invention is defined by the claims and their equivalents.

The disclosed system further provides functionality for adding and managing pharmacy profiles, such as providing customer service information including patient contact and coverage information, services offered by pharmacies, and maps and directions to the pharmacies.

Other embodiments of the invention will be apparent to those skilled in the art from consideration of the specification and practice of the invention disclosed herein. The specification and examples should be considered as exemplary only, with a true scope and spirit of the invention being indicated by the following claims.

What is claimed is:

1. A method for managing prescriptions, the method comprising:
   receiving a patient assessment from a physician at an application server;
   receiving a prescription based on the patient assessment at the application server;
   determining drug interactions at the application server based on the received prescription;
   sending the prescription from the application server to a pharmacy based on the drug interaction determination; and
   validating the prescription based on the sent prescription and patient assessment,
   wherein receiving a patient assessment from a physician at an application server comprises receiving an access request at an application server from a remote device, receiving at least one of a physician identification number and a physician password at the application sewer, validating a physician identity based on the received identification number and the password, receiving a patient identification number at the application server, and sending patient information to the remote device in response to the received patient identification number.

2. The method of claim 1 further comprising:
   storing the patient assessment in a centralized database in communication with the application server.

3. The method of claim 1 further comprising:
   storing the prescription in a centralized database operably connected with the application server.

4. The method of claim 1 wherein determining drug interactions comprises comparing the received prescription with a plurality of patient medical records stored on a centralized database operably connected to the application server.

5. The method of claim 1 further comprising:
setting an Rx flag status indicator to an ordered designation based on sending the prescription to the pharmacy.

6. The method of claim 1 further comprising filling the prescription at the pharmacy.

7. The method of claim 6 wherein validating the prescription comprises comparing the filled prescription to a bulk medicine container and to the received prescription.

8. The method of claim 7 further comprising:
setting an Rx flag status indicator to a filled designation based on the validation of the prescription.

9. The method of claim 1 wherein determining drug interactions comprises comparing the received prescription with a plurality of patient medical records stored on a centralized database operably connected to the application server.

10. The method of claim 1 further comprising:
storing the received prescription information in a centralized database.

11. The method of claim 1 further comprising:
setting an Rx flag status indicator to an ordered designation based on sending the prescription to the pharmacy.

12. The method of claim 1 further comprising:
receiving a pharmacy location at the application server and sending the prescription information to the pharmacy.

13. The method of claim 12 farther comprising:
validating the prescription at the pharmacy.

14. The method of claim 13 farther comprising filling the prescription at the pharmacy.

15. The method of claim 14 wherein validating the prescription comprises comparing the filled prescription to a bulk medicine container and to the received prescription information.

16. The method of claim 15 farther comprising:
setting an Rx flag status indicator to a filled designation based on the validation of the prescription.

* * * * *